United States Patent [19]

Hanson

[11] Patent Number: 4,736,044

[45] Date of Patent: Apr. 5, 1988

[54] BORON COMPOUNDS TO INHIBIT FORMATION OF TAR DURING THE "ENE" REACTION OF AN ETHYLENICALLY UNSATURATED ALPHA, BETA DICARBOXYLIC ACID COMPOUND AND AN ETHYLENICALLY UNSATURATED HYDROCARBON

[75] Inventor: Joseph B. Hanson, Wheaton, Ill.

[73] Assignee: Amoco Corporation, Chicago, Ill.

[21] Appl. No.: 551,181

[22] Filed: Nov. 14, 1983

Related U.S. Application Data

[63] Continuation of Ser. No. 341,951, Jan. 21, 1982, abandoned, which is a continuation of Ser. No. 50,462, Jun. 20, 1979, abandoned.

[51] Int. Cl.$^4$ ........................................... C07D 307/60
[52] U.S. Cl. .................................. 549/255; 549/203; 562/489; 562/509; 562/578; 562/582; 562/594; 562/595
[58] Field of Search ............... 562/595, 489, 578, 509, 562/594, 582; 549/255, 203

[56]  References Cited

U.S. PATENT DOCUMENTS 3,022,321  2/1962  Copenhaver .................... 562/509
4,086,251  4/1978  Cengel et al. ................... 549/255
4,235,786  11/1980 Wisotsky ......................... 549/255
4,257,958  3/1981  Powell ............................. 549/255

FOREIGN PATENT DOCUMENTS

F10267  9/1956  Fed. Rep. of Germany ...... 562/595

Primary Examiner—Vivian Garner
Attorney, Agent, or Firm—Richard A. Kretchmer; William H. Magidson

[57]  ABSTRACT

A process for the production of a substituted alpha, beta dicarboxylic acid compound substantially free of tar and other resinous reaction byproducts comprising the reaction at conditions favoring the ENE reaction of an ethylenically unsaturated hydrocarbon and an ethylenically unsaturated alpha, beta dicarboxylic acid compound in the presence of a boron compound.

12 Claims, No Drawings

BORON COMPOUNDS TO INHIBIT FORMATION OF TAR DURING THE "ENE" REACTION OF AN ETHYLENICALLY UNSATURATED ALPHA, BETA DICARBOXYLIC ACID COMPOUND AND AN ETHYLENICALLY UNSATURATED HYDROCARBON

This is a combination of application Ser. No. 341,451, filed Jan. 21, 1982, which is a continuation of application Ser. No. 50,462, filed June 20, 1979, both abandoned.

This invention relates to a process for the production of a substantially tar-free "ENE" reaction product of an ethylenically unsaturated alpha, beta dicarboxylic acid compound and an ethylenically unsaturated hydrocarbon. More particularly this invention relates to a process using boron compounds as an agent to reduce the formation of tar and other resinous by-products during the "ENE" reaction of an ethylenically unsaturated hydrocarbon and ethylenically-unsaturated alpha, beta dicarboxylic acid compound, said tar being substantially a thermal decomposition product of the unsaturated dicarboxylic acid compound.

The "ENE" reaction products can be used for a variety of purposes such as in adhesives, insulating oils, as a raw material in the production of synthetic lubricating oils, preservatives, polyesters, additives in lubricants and fuels, etc. A very important use of these products is as a raw material for the manufacture of additives to improve the characteristics of fuels and lubricants. Most commonly, the reaction product of a substituted dicarboxylic acid compound, and an amine compound such as a polyamine, can be used in gasolines and lubricants. These additives having a number average molecular weight less than 500 are often useful in fuels such as gasolines to inhibit rust, carburetor deposits, carburetor icing, etc. Addition agents having a number average molecular weight in excess of about 500 have found extensive use as dispersants in motor oils to prevent the formation of harmful deposits on engine surfaces caused by oxidation products of lubricants, fuels, wear products, ingested dirt, etc.

The Diels-Alder "ENE" reaction between an ethylenically unsaturated hydrocarbon and an alpha, beta unsaturated dicarboxylic acid compound involves the addition of the unsaturated hydrocarbon to the unsaturated dicarboxylic acid. An example of the reaction is the addition of polyisobutylene to maleic anhydride:

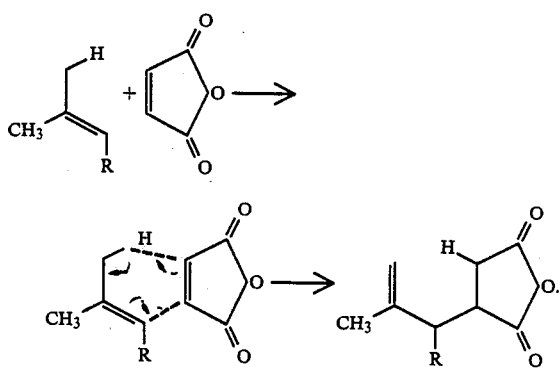

The uncatalyzed "ENE" reaction between an ethylenically unsaturated hydrocarbon and an ethylenically unsaturated alpha, beta dicarboxylic acid compound has a major drawback. The unsaturated dicarboxylic acid compound suffers thermal decomposition causing the formation of tar and other resinous byproducts. Thermal decomposition of ethylenically unsaturated alpha, beta dicarboxylic acid compounds at temperatures in excess of 100° C. has been known and reported, for example, in U.S. Pat. No. 3,476,774. Such thermal decomposition can be accompanied by the evolution of water vapor and oxides of carbon. Under some observed conditions, the thermal decomposition can be explosive. In the absence of explosive decomposition, the thermal decomposition of the reactants and reaction products form carbon containing residues which are manifest in granular and tarry forms. Since the granular residue tends to remain suspended in the reaction product and cannot be removed easily therefrom, the desired product is often commercially unacceptable. The resinous tar-like residue tends to coat the internal surface of the reaction vessel, thereby necessitating the periodic shutdown and cleaning of the tarry material from the reactors. The destruction of the ethylenically unsaturated alpha, beta dicarboxylic acid compound by thermal decomposition is also economically undesirable.

A variety of tar and resinous byproduct inhibitors for the "ENE" reaction have been proposed by the prior art. In general there are at least three types of inhibitors: (1) substituted benzene sulfonic acids, (2) halogenated compounds such as halogenated polymers, dibromohydantoin, and (3) phenothiazine and quinone-type compounds. The substituted benzene sulfonic acid-type inhibitors suffer the drawbacks that the sulfonic acid is acidic and poses a corrosion hazard to operators and production equipment used in the production of the substituted succinic anhydride. Sulfonic acids are also known to cause isomerization of the dicarboxylic acid and reduced production of product. The halogenated organic compound-type inhibitor has the drawback that these inhibitors leave halide contamination in the product and pose a slight corrosion hazard to both personnel and processing equipment. The phenothiazine and quinone-type inhibitors are relatively expensive.

Clearly a need exists for a noncorrosive, inexpensive, highly active tar and resinous byproduct inhibitor for the "ENE" reaction of ethylenically unsaturated alpha, beta dicarboxylic acid compounds.

The primary object of this invention is to improve the "ENE" reaction of an ethylenically unsaturated hydrocarbon and an ethylenically unsaturated alpha, beta dicarboxylic acid compound. Another object of the invention is to reduce the formation of tar and other resinous byproducts during the "ENE" reaction. Other objects of the invention appear hereinafter.

I have found that the "ENE" reaction of an ethylenically unsaturated hydrocarbon and an ethylenically unsaturated alpha, beta dicarboxylic acid compound can be improved by the the presence of an effective amount of a boron compound. The boron compound apparently stabilizes the ethylenically unsaturated alpha, beta dicarboxylic acid compound to thermal decomposition preventing the formation of tar and other resinous byproducts.

Briefly, the process of the invention is performed by reacting an ethylenically unsaturated hydrocarbon with an unsaturated alpha, beta dicarboxylic acid compound under "ENE" reaction conditions in the presence of an effective amount of a boron compound.

Boron compounds useful for the production of substituted dicarboxylic anhydrides include boric acid, boric acid salts such as ammonium borate, amine salts of boric acid, sodium borate, potassium borate, calcium borate, magnesium borate, meta borates, etc., boron oxides such as $B_2O_3$, etc., boron salts such as boron arsenate, borohydride compounds such as diborane, dihydrotetraborane, pentaborane, hexaborane, organo boron compounds such as trialkyl borate or trialkoxy boron, for example trimethyl borate, triethylborate, diethyl propyl borate, triisopropyl borate, tri-t-butyl borate, tridecyl borate, etc, and other organo boron compounds such as aryl boronic acids, triaryl boroxene, trimethylborane, amino-borane compounds, and borazene. For reasons of high activity and low cost, boric acid ($H_3BO_3$), boric acid salts, and boron oxide are preferred boron compounds Ethylenically unsaturated hydrocarbon useful in the ENE reaction of this invention are substantially hydrocarbon compounds containing from about 10 to about 430 carbon atoms containing from about 1 to about 4 olefinic bonds. The olefinic compounds can contain other functional groups such as hydroxyls, carbonyls, carboxyl groups, halide groups, alkyl and aryl substituents, nitrogen-containing groups, organometallic groups, sulfur containing groups, etc. The important characteristics of the alkene is that at least one ethylenically unsaturated group with at least one allylic hydrogen atom, is present for the "ENE" reaction. In the absence of the allylic hydrogen the olefin must be capable of isomerizing under reaction conditions to an olefin containing an allylic hydrogen substituent. Substituents which increase the electron density of the double bond also facilitate the reaction. Suitable ethylenically unsaturated hydrocarbons include decene, isodecene, dodecene, tertiary dodecene, 2-ethyldecene, eicosene, pentacontene, etc. can be used. These compounds can be derived directly from refinery streams, or can be produced by the oligomerization of olefins such as ethene, propene, or butene. Other ethyleneically unsaturated hydrocarbons that can be used are polymers produced by the polymerization of common olefinic monomers such as ethene, propene, 1-butene, 2-butene, and isobutylene. These polymers commonly have a molecular weight from about 140 to about 6,000 produced by commercial well-known polymerization techniques.

Preferably for reasons of availability, low cost, and high reactivity, viscous polyalkene polymers of olefinic monomers are preferred. These polymers can contain up to about 430 carbon atoms and are prepared from alkene monomers such as ethene, propene, 1-butene, cis- and trans-2-butene, and isobutylene. The viscous polyalkene polymers are commonly produced by the polymerization of the alkene stream under pressure in contact with an aluminum chloride catalyst. The preferred polyalkenes for reasons of high activity and low cost are polypropene, polyisobutylene and polybutene having a molecular weight between 140 and about 6,000, preferably for ease of reaction and high activity, a molecular weight of about 200 to about 3,000 is used.

Ethylenically unsaturated alpha, beta dicarboxylic acid compounds useful in the "ENE" reaction include maleic anhydride, maleic acid, fumaric acid, citraconic anhydride, citraconic acid, itaconic anhydride, itaconic acid, ethyl maleic anhydride, ethyl maleic acid, halo- (e.g., chloro) maleic anhdride, etc. Preferably, for ease of reaction and low cost, maleic acid or maleic anhydride can be used.

In somewhat greater detail, the "ENE" reaction between the ethylenically unsaturated hydrocarbon and the ethylenically unsaturated alpha, beta dicarboxylic acid compound is carried out in standard commercial well-known procedures. The art recognizes both batchwise reaction or continuous reaction in stirred tanks, pressurized reactors, continuous reaction zones, or other equivalent reaction vessels to provide intimate contact between the reactants.

For batchwise operation the reactants are charged to the closed reaction vessel with or without an inert (oxygen-free) atmosphere at ambient or elevated pressure. The reactants can be added to the vessel at ambient temperature. However, the ethylenically unsaturated hydrocarbon can be used at an elevated temperature to reduce the time for reaction and to reduce viscosity. The ethylenically unsaturated alpha, beta dicarboxylic acid compound can be charged in solid form or dispersed in a portion of the unsaturated hydrocarbon or can be heated and added to the reactant mixture as a melt. During the reaction the mixture is stirred while the reaction temperature is controlled. Convenient conduct of the reaction can be maintained by charging to the reaction vessel a melt of the ethylenically unsaturated alpha, beta dicarboxylic acid compound and preheated ethylenically unsaturated hydrocarbon so that the combined reactants provide sufficient heat to drive the reaction. At the end of the reaction, excess dicarboxylic acid compound can be removed by distillation. The product which can contain minor amounts of unsaturated hydrocarbon can be filtered and used. Reaction time for batchwise operation can be 4 to 24 hours and greater.

In continuous operation, ambient or heated streams of dicarboxylic acid compound and unsaturated hydrocarbon can be charged to one end of a horizontal or vertical reaction zone. The reactants can be intimately contacted within the zone for a sufficient time at a sufficient temperature and pressure. The product can be withdrawn from the zone to appropriate strippers and filters. In order to maximize conversions of the reactant and to minimize formation of solid or tarry or resinous degradation products, the reaction can be carried out with a continuous dicarboxylic acid compound reflux. The reflux rate can be in slight excess of the reaction requirements for the dicarboxylic acid compound. In this way the reaction solution is kept saturated with dicarboxylic acid compound throughout the reaction. Any dicarboxylic acid compound in excess over that required to saturate the reaction zone continuously distills from the reaction zone overhead avoiding the appearance of separate dicarboxylic acid compound phase in the reactor and the consequent contamination of the reaction product. The reduction in the concentration of the dicarboxylic acid compound also reduces the products of degradation. The unsaturated hydrocarbon feed can also be controlled so that the rate of reflux and the feed rate of the unsaturated hydrocarbon are balanced to match the stoichiometric ratio of reactants. In continuous operation a shorter residence time is possible, for example, 1 to 8 hours.

The boron compound can be added to the reaction in any convenient manner. For example, the boron compound can be suspended or dissolved in either reactant stream. Alternatively, the boron compound can be directly added to the reactor or can be dissolved in an inert solvent such as pentane, heptane, gasoline, kerosene, lubricating oil fractions, benzene, toluene, etc., prior to addition.

The boron compound can be used in the reaction at concentrations of from about 1.0 to about 100,000 parts by weight per million parts by weight of the ethylenically unsaturated hydrocarbon reactant. The boron compound can be used in conjunction with a variety of other process aids or catalysts with somewhat poorer results such as the alkylated benzene sulfonic acids, the halogenated reaction promoters, or the phenothiazine or other processes or catalysts described in the art for this reaction. Preferably, the boron compound is present in the reaction at a concentration of about 100 to 1,000 parts by weight of the boron compound per million parts by weight of the unsaturated hydrocarbon to conserve boron compound and to efficiently reduce the production of tarry and other resinous byproducts.

Commonly the reaction can be run at molar ratios of about 0.5 to about 10 moles of ethylenically unsaturated alpha, beta dicarboxylic acid compound per mole of ethylenically unsaturated hydrocarbon. Preferably, the reaction is run with a slight excess of ethylenically unsaturated hydrocarbon. For example, from about 1 to about 1.5 moles of unsaturated hydrocarbon is reacted with about 1 mole of unsaturated dicarboxylic acid compound. This slight excess promotes complete reaction and reduces the residual unsaturated hydrocarbon left in the product. The reaction can be run at ambient to high pressure at temperatures from about 100° C. to about 300° C. However, to maintain viscosity control of reactants while minimizing the thermal decomposition of the ethylenically unsaturated alpha, beta dicarboxylic acid compound, the reaction mixture is maintained at a temperature of from about 200° to 250° C.

While the applicant does not wish to be limited to any theory of the action of the boron compound, the boron compound during the reaction apparently reacts with and stabilizes the unsaturated dicarboxylic acid compound to thermal decomposition while activating the unsaturated dicarboxylic acid compound to promote the "ENE" reaction.

The following examples are illustrative and should not be construed as limiting the scope of the invention.

EXAMPLE I

Into a three-neck pyrex round bottom flask fitted with a heating mantle, mechanical stirrer, temperature controller, nitrogen purge tube, heated addition funnel and condenser were placed 919 grams (1 mole) of a viscous polybutene having a molecular weight of about 1,022. Into the heated addition funnel was weighed 84.3 grams (0.86 moles) of maleic anhydride. The maleic anhydride was heated and maintained molten in the funnel. Two and three-tenths grams (0.04 moles) of boric acid ($H_3BO_3$) were added as a solid powder to the polymer in the flask. The contents of the flask were stirred and heated to 215° C. Volatiles driven off the polymer and boric acid were swept from the flask by the nitrogen purge. The molten maleic anhydride in the heated addition funnel was added to the polybutene in small increments over a four-hour period. The reaction mixture was maintained at 215° C. for about 18 hours. At the end of this period, the temperature of the flask was raised to 238° C. and nitrogen gas at two standard cubic feet per hour was passed through the flask to strip unreacted maleic anhydride. After two hours of stripping, the reaction mixture was cooled to about 150° C. and filtered through celite. To determine the amount of insoluble tar residue produced during the reaction, the flask and other pieces of reaction assembly were weighed prior to reaction. After reaction the assembly was carefully rinsed with hexane and dried. The assembly was reweighed to determine the amount of tar and other deposits adhering to the interior of the assembly.

EXAMPLE II

Example I was repeated except that the reaction was run with 1,022 grams polybutene and 2.5 grams boric acid at a temperature of about 235° C.

EXAMPLE III

Example II was repeated except that the reaction was run with 1,022 grams polybutene and 1 gram (0.014 moles) of boric oxide ($B_2O_3$) was substituted for the boric acid.

EXAMPLE IV

Example II was repeated except that the reaction was run with 1,022 grams polybutene and 2.5 grams (0.35 moles) of boric oxide were substituted for the boric acid.

EXAMPLE V

Example I was repeated except that about 1 gram (0.01 moles) of tributylborate was substituted for the boric acid.

EXAMPLE VI

Example I was repeated except that 1.4 grams of paratoluene sulfonic acid dissolved in 2.8 grams acetic anhydride were substituted for the boric acid.

EXAMPLE VII

Example VI was repeated except that the reaction was run at a temperature of about 235° C. instead of 215° C.

EXAMPLE VIII

Example I was repeated except that dibromohydantoin was added to the reaction mixture in place of the boric acid at a final concentration of about 0.02% by weight based on the reaction mixture.

EXAMPLE IX

Example VIII was repeated except that the reaction was run with 1,022 grams polybutene and the reaction was run at 235° C.

EXAMPLE X

Example I was repeated without the boric acid.

EXAMPLE XI

Example X was repeated except that the reaction was run with 1,022 grams polybutene and the reaction temperature was 235° C.

Table I displays the results of the reactions between the alkene and the maleic anhydride in the presence of the variety of inhibitors as done in Examples I–XI. The amount of tar listed was determined by weighing the reaction equipment prior to the reaction of the alkene and the maleic anhydride, performing the reaction, removing the succinic anhydride product, rinsing with hexane, drying, and reweighing the reaction vessels to determine the amount of insoluble tar adhering to the interior surfaces of the reaction vessel.

TABLE I

TAR INHIBITION

| EXAMPLE | INHIBITOR | REACTION TEMP (°C.) | INHIBITOR WT (%) (CONC.)[1] | WT (%) TAR[1] |
|---|---|---|---|---|
| I | $H_3BO_3$ | 215 | 0.25 | 0.08 |
| II | $H_3BO_3$ | 235 | 0.25 | 0.04 |
| III | $B_2O_3$ | 235 | 0.10 | 0.04 |
| IV | $B_2O_3$ | 235 | 0.25 | 0.20 |
| V | $B(OC_3H_8)_3$ | 215 | 0.10 | 0.11 |
| VI | Paratoluene sulfonic acid | 215 | 0.15 | 0.15 |
| VII | Paratoluene sulfonic acid | 235 | 0.15 | 0.09 |
| VIII | Dibromo-dimethyl-hydantoin | 215 | 0.02 | 0.04 |
| IX | Dibromo-dimethyl-hydantoin | 235 | 0.02 | 0.05 |
| X | None (blank) | 215 | — | 0.4 |
| XI | None (blank) | 235 | — | 0.6 |

[1](wt) % based on weight of alkene.

Table I reveals that the boron compound inhibitors provide a high level of tar inhibition during the reaction at low concentrations.

The foregoing specification is a detailed explanation illustrative of the Applicant's invention. However, the Applicant's invention resides in the claims appended hereinafter.

I claim:

1. A process for the production of a substituted alpha, beta dicarboxylic acid compound which comprises the reaction at conditions favoring the "ENE" reaction of maleic anhydride with an ethylenically unsaturated hydrocarbon in the presence of an effective tar and resinous reaction by-product reducing amount of a boron compound which is selected from the group consisting of boric acid, boric oxide, and trialkyl borates.

2. The process of claim 1 wherein the boron compound is present in the reaction mixture at a concentration of about 1 to 100,000 parts by weight per million parts by weight of unsaturated hydrocarbon compound.

3. The process of claim 1 wherein the ethylenically unsaturated hydrocarbon comprises a substantially linear hydrocarbon having a molecular weight of from 140 to 6,000.

4. The process of claim 3 wherein the ethylenically unsaturated hydrocarbon comprises polyisobutylene or polypropene.

5. A process for the production of a substituted succinic acid compound which comprises the reaction at conditions favoring the "ENE" reaction of polybutene with maleic anhydride in the presence of an effective tar and resinous reaction by-product reducing amount of a boron compound selected from the group consisting of boric acid, boric oxide, and trialkyl borates.

6. The process of claim 5 wherein the boron compound is present at a concentration of about 1 to 100,000 parts by weight of boron compound per million parts by weight of ethylenically unsaturated hydrocarbon.

7. A process as set forth in claim 5 wherein said polybutene has a molecular weight in the range from about 200 to about 3,000.

8. A process as set forth in claim 7 wherein said boron compound is selected from the group consisting of boric acid and boric oxide.

9. A process as set forth in claim 8 wherein said reaction is carried out at a temperature in the range from about 100° C. to about 300° C.

10. A process as set forth in claim 9 wherein the amount of said boron compound is from about 100 to 1,000 parts by weight per million parts by weight of polybutene.

11. A process as set forth in claim 7 wherein said boron compound is tributylborate.

12. A process as set forth in claim 7 wherein the molar ratio of maleic anhydride to polybutene is in the range from about 0.5:1 to about 10:1.

* * * * *